(12) United States Patent
Leonard et al.

(10) Patent No.: US 6,503,459 B1
(45) Date of Patent: Jan. 7, 2003

(54) HEATED VOLATILE DISPENSER

(75) Inventors: Stephen B. Leonard, Caledonia, WI (US); Scott W. Demarest, Caledonia, WI (US); Michael C. Fryan, Mount Pleasant, WI (US); Donald J. Shanklin, Fullerton, CA (US); Paul E. Furner, Caledonia, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/335,370

(22) Filed: Jun. 17, 1999

(51) Int. Cl.$^7$ ................................................ A62B 7/08
(52) U.S. Cl. ............................. 422/125; 422/4; 422/5; 422/120; 422/123; 422/126; 431/344
(58) Field of Search ............................... 126/248, 249, 126/250, 251, 252, 253, 254, 255; 431/344, 4, 5, 120, 123; 422/125, 126

(56) References Cited

U.S. PATENT DOCUMENTS

| | | | |
|---|---|---|---|
| 143,583 A | 10/1873 | Mayall | |
| 323,547 A | 8/1885 | Valentire | |
| 382,836 A | 5/1888 | Sheeley | |
| 611,560 A | 9/1898 | Chambers | |
| 630,401 A | * 8/1899 | Page | 422/125 |
| 692,075 A | 1/1902 | Searle | |
| 746,942 A | 12/1903 | Feval | |
| 1,243,439 A | 10/1917 | Myers | |
| 1,732,707 A | 10/1929 | Winsboro | |
| 1,817,057 A | * 8/1931 | Berry | 422/125 |
| 1,920,599 A | 8/1933 | Schuh | |
| 2,451,238 A | 10/1948 | Pritchard | |
| 2,510,449 A | * 6/1950 | Williams et al. | 422/125 |
| 2,513,919 A | 7/1950 | Costello | 219/19 |
| 2,519,544 A | 8/1950 | Churchill | 67/23 |
| 2,611,068 A | 9/1952 | Wellens | 219/19 |
| 2,714,649 A | 8/1955 | Critzer | 219/19 |
| 2,742,342 A | 4/1956 | Dew et al. | 21/53 |

(List continued on next page.)

FOREIGN PATENT DOCUMENTS

| | | |
|---|---|---|
| DE | 1 691 197 | 1/1955 |
| DE | 1023625 | 1/1958 |
| DE | 297 20 802 U1 | 11/1997 |
| DE | 29720 802 U1 | 5/1998 |
| FR | 2537394 | 12/1983 |
| JP | 48101 * | 6/1993 |
| JP | HEISEI 5-48101 | 6/1993 |
| JP | 10-162611 | 6/1998 |
| WO | WO 92/06594 | 4/1992 |
| WO | WO 99/51912 | 10/1999 |
| ZA | A 94/5537 | 10/1996 |

OTHER PUBLICATIONS

Patent Abstract of Japan, Publication No. 08–311464.
Patent Abstract of Japan, Publication No. 10–162611.

(List continued on next page.)

*Primary Examiner*—Robert J. Warden, Sr.
*Assistant Examiner*—Imad Soubra

(57) ABSTRACT

A heated volatile dispenser and a volatile carrier for use therewith are disclosed. The volatile dispenser has a closed heating chamber having ceiling and exit vents. A fuel burner is contained within the heating chamber, and a carrier holder is positioned over the fuel burner. The carrier holder holds a volatile carrier in a location above the fuel burner such that hot combustion products from the fuel burner pass the carrier holder and directly heat a volatile carrier held thereby. The volatile carrier may be held in an edge-on orientation with respect to the flow of hot gases, or transversely with respect to them. The volatile carrier has an inward end that has a cross-sectional profile made to be complementary to that of an insert slot through which the volatile carrier must be inserted for use. Methods of dispensing volatiles are disclosed.

36 Claims, 8 Drawing Sheets

U.S. PATENT DOCUMENTS

| | | | |
|---|---|---|---|
| 2,757,278 A | 7/1956 | Cloud | 240/73 |
| 2,813,187 A | 11/1957 | Rovira | 219/19 |
| 2,942,090 A | 6/1960 | Diehl | 219/19 |
| 3,279,118 A | 10/1966 | Allen | 43/129 |
| 3,778,924 A | 12/1973 | Okui | 43/129 |
| 4,251,714 A | 2/1981 | Zobele | 219/275 |
| 4,321,656 A | 3/1982 | Gruver, Jr. | 362/180 |
| 4,627,963 A | 12/1986 | Olson | 422/125 |
| 4,745,705 A | 5/1988 | Yamamoto et al. | 43/125 |
| 4,750,471 A | 6/1988 | Hautmann et al. | |
| 4,781,895 A | 11/1988 | Spector | 422/125 |
| 4,839,144 A | 6/1989 | Martin | 422/305 |
| 4,849,181 A | 7/1989 | Kelley et al. | 422/126 |
| 5,111,477 A | 5/1992 | Murderlak | 392/390 |
| 5,460,787 A * | 10/1995 | Colon | 422/125 |
| 5,478,505 A * | 12/1995 | McElfresh et al. | 422/124 |
| 5,700,430 A | 12/1997 | Bonnema et al. | |
| 5,722,199 A | 3/1998 | Demarest et al. | 43/113 |
| 5,744,106 A | 4/1998 | Eagle | 422/306 |
| 5,827,483 A * | 10/1998 | Fullam | 422/125 |
| 5,911,955 A * | 6/1999 | Fullam | 422/125 |
| 6,033,212 A | 3/2000 | Bonnema et al. | |

OTHER PUBLICATIONS 3 pages depicting the Skeeter Eater mosquito destroyer unit, undated, admitted prior art (see page 3 of the specification).

4 pages depicting a Japanses insect control unit, undated, admitted prior art, supplier unknown (see page 3 of the specification).

1 page depicting another insect control unit, undated, admitted prior art, supplier unknown (see page 3 of the specification).

1 page with photographs of another insect control unit, undated, admitted prior art, a commercial version of the product described in South African appln. 94/5537.

* cited by examiner

HEATED VOLATILE DISPENSER

CROSS-REFERENCE TO RELATED APPLICATIONS

Not Applicable

STATEMENT REGARDING FEDERALLY SPONSORED RESEARCH/DEVELOPMENT

Not Applicable

BACKGROUND OF THE INVENTION

The present invention relates to dispensers for volatiles such as scents, insect control active ingredients, and the like. In particular, it relates to such dispensers that use a fuel burner.

There are a variety of known dispensers for volatiles that employ heat from a flame or from catalyzed combustion to dispense volatiles from volatile-impregnated substrates. Citronella candles mix the volatile into the fuel itself. However, this leaves the candle flame exposed.

U.S. Pat. No. 692,075 shows the use of heat from the flame of a conventional oil lamp to dispense volatile ingredients held exposed to the ambient air on a mesh mounted on a lamp chimney, above the lamp's flame. The disclosure of this patent and of all other publications referred to herein are incorporated by reference as if fully set forth herein. The volatile material being heated by this device is positioned above the lamp chimney and thus is directly exposed to ambient air currents, which can cause uneven heating and cooling of the volatile material. The exposed location of the material being heated also allows it to be touched or disturbed by a passing child or animal. Furthermore, it is immediately visible to a user so that charred material can present an unsavory sight.

U.S. Pat. No. 143,583 discloses a fumigator in which an alcohol lamp is placed at the bottom of a metal chimney. A cup to hold an otherwise uncontained liquid fumigant is suspended within the chimney at its top, and a perforated lid closes the chimney. The lamp heats the liquid fumigant, and vapor escapes through the perforations of the lid. Handling the uncontained liquid fumigant and gaining access to and refilling the cup can be inconvenient and risk spillage.

Petzwinkler, South African patent abstract 94/5537, discloses an oil lamp equipped with a metal mosquito mat holder that is positioned beside, as opposed to over, the lamp's flame. Heating radiating from the flame heats a metal holder from that side of the holder which is presented toward the flame. A conventional mosquito mat is then held vertically on the opposite side of the holder, away from the flame. By this means, the mat is shielded from direct exposure to the flame or its combustion products, albeit it is heated to drive off the volatiles contained in the mat.

The Petzwinkler dispenser provides a visible flame. However, this dispenser has a mosquito mat holder that holds a mat beside the flame, in open view of a user, detracting from the pleasing visual effect of the flame itself. Also, one must remove the dispenser's chimney to gain access to a spent mat to replace it.

U.S. Pat. Nos. 5,700,430 and 3,778,924 each employ butane as a fuel for a flame or a catalytic burner, using a replaceable fuel tank. In U.S. Pat. No. 5,700,430 a mosquito mat is laid on top of a metal plate. Heat is conducted from the location of a flame to the metal plate by means of intervening, heat-conductive parts. In a subsequent version of the device that otherwise closely corresponded to the embodiment shown, a butane flame was enclosed within a metal, rectangular, open-ended box. The box was heated by the flame, and the flame's combustion products exited an open end of the box to be vented from the device. A mosquito mat was positioned on top of the box to receive heat conducted through the metal box from the flame. The butane flame, heat-conductive parts, and mosquito mat were all held within a protective heat box.

U.S. Pat. No. 5,700,430 thus relies on indirect heating. The volatiles from the hottest places on the mat are released fastest. Consequently, the mat's volatiles are discharged unevenly, with the possibility that volatiles at locations remote from the attachment point may never be discharged before the mat's overall release rate becomes so low as to require replacement of the mat.

In U.S. Pat. No. 3,778,924 a mosquito mat is held exposed to the ambient air on a metal sole plate over a catalytic burner fueled by butane drawn from a replaceable, pressurized tank. However, the mat is not enclosed in a heating chamber.

Other patents disclose assemblies that rely on an electrical heater (as distinguished from a fuel burning heater) to heat the volatile carrier. See e.g. U.S. Pat. Nos. 2,513,919, 2,942,090, 4,849,181 and 5,111,477. This restricts the portability of the device (it cannot easily be used at camping or picnic sites which do not have electrical power).

U.S. Pat. No. 5,722,199 discloses a flea trap (without a volatile heater) having a removable tray that slides into a slot in the flea trap. The slot has keying structures that restrict access into the slot. To enter, a tray must present a complementary cross-sectional profile to the slot.

There are also a number of other known insect repellent/killing devices which provide a heat source under a platform designed to support a pad that has been impregnated with the insect control active ingredient. Some use a liquid fuel such as alcohol that is burned in an open flame, or directed to a catalyst mesh where it combusts.

In some cases the platform is an open grid. In others it is a flat metal plate heated from beneath. Some of these systems also provide a separate grid structure which snaps or swings over the carrier for restricting access to the heated mat during operation. These systems typically do not provide a light source through transparent sides of a heating chamber (e.g. they are designed purely for insect control).

It can therefore be seen that there is a need for an improved heated volatile dispenser.

BRIEF SUMMARY OF THE INVENTION

The invention provides a heated volatile dispenser for dispensing volatile ingredients from a volatile carrier. "Volatile ingredients" include (without limitation) perfumes and other air quality modifying materials, as well as insect control ingredients. "Insect" includes arachnids and other similar, small animals commonly controlled in conjunction with insects. "Insect control ingredients" are defined as including (without limitation) insecticides, repellents, and other development or behavior modifying materials. One highly preferred insect control agent is d-cis/trans allethrin.

A "volatile carrier" is a material or structure for holding a volatile ingredient for dispensing. "Mats" are one common type of volatile carrier often used with insect control ingredients and are defined as including (without limitation) woven, felted, or otherwise formed fibrous or cellulose materials; as well as molded, extruded, cast, or otherwise formed polymeric, ceramic, and clay materials, together with other convenient materials loaded with volatile ingredients, whether by impregnation, printing, or otherwise. Volatile carriers can also be metal or plastic cups holding a volatilizable gel, cups holding a gel, powder, or liquid retained in the cup by a volatile-permeable membrane, or any other convenient means for holding a material to be volatilized by the application of heat. However, uncontained liquids or powders, together with liquids or powders held in open cups or similar containers, are excluded from the term "volatile carrier", as used herein.

In one form, the heated volatile dispenser of the invention has an enclosed heating chamber having chamber walls, a ceiling, and exit vents in the ceiling or chamber walls or both, the exit vents communicating between the interior of the heating chamber and the outside air. A heating chamber will be understood as being "enclosed" if it has solid walls and a solid ceiling and either a closed or an open bottom, one or both of the ceiling and walls being equipped with holes, slots, or other vents. Particularly preferred are permanently enclosed structures.

The dispenser also has a heat source that preferably is a fuel burner. The fuel burner can be a candle, a burner using a solidified combustible liquid such as conventional gelled alcohol, a burnable solid, a pressurized gas burner, a wick that is fueled with a combustible liquid, a catalytic heater burning a gas or liquid fuel, or any other convenient means for combusting a fuel.

The heated volatile dispenser also includes a carrier holder that is positioned to receive and hold a volatile carrier at a location above the fuel burner and contained within the heating chamber. An air-flow path is provided to guide hot gases, rising from the fuel burner by convection, past the carrier holder to heat a volatile carrier held in the carrier holder. The air-flow path is preferably defined, at least in part, by internal surfaces of the heating chamber walls. Heating is accomplished by the direct exposure of the volatile carrier to gases heated by the fuel burner. Preferably, the hot gases include hot combustion products from the fuel burner. The air-flow path then directs the hot combustion products through the exit vents to escape from the dispenser. As the volatile carrier is heated by the gases, volatile material is released and is carried out of the dispenser with the escaping hot gases.

In one form the carrier holder can be a slot in the chamber wall through which a volatile carrier is inserted, with the slot being a sufficiently snug fit for the volatile carrier that the parts of the volatile carrier projecting within the heating chamber are held in position by the snug contact between the slot and the volatile carrier. Also, a possible carrier holder can be a slot in the heating chamber ceiling, for use with a volatile carrier that is designed to be inserted downwardly through the slot and to hang from the edges of the slot from side tabs, a handle, or other parts of the volatile carrier that, because of their size or geometry, remain outside of the heating chamber, resting on outer surfaces of the ceiling.

Alternatively, the carrier holder may be an essentially open, either vertically or horizontally disposed, rack that leaves the mat or other volatile carrier held in the carrier holder directly exposed to hot gases rising in a convective flow from beneath. Alternatively, the carrier holder can be a generally horizontal heat-conductive sole plate that supports the volatile carrier. While the upper surface of the volatile carrier remains directly exposed to the hot gases from the fuel burner, the under surface of the volatile carrier is in contact with and heated by the sole plate, with the under side of the sole plate being exposed to the flow of hot combustion products from the fuel burner or to heat otherwise received from the fuel burner.

Depending on the materials chosen and the carrier temperatures desired, it is also possible to include a baffle spaced from and preferably located beneath the carrier holder and interposed between the fuel burner and a volatile carrier being held in the carrier holder. The baffle functions in part to mix hot combustion products from the fuel burner with air in the heating chamber prior to their reaching the volatile carrier. The result is believed to be a reduction of the tendency for a hot spot to form at a point on the volatile carrier directly above the fuel burner. Instead, the baffle causes a more even heating of the volatile carrier, whether the volatile carrier is heated solely by direct exposure to the hot gases or by a combination of direct exposure to hot gases and heat conducted through a sole plate.

The baffle can also function to more evenly distribute heat in another way. If the baffle is so located as to be heated by hot gases contacting the baffle from below, and if the carrier holder is spaced above the baffle, then the hot baffle serves as a radiant heater, supplementing heat delivered by a volatile carrier's direct contact with the hot gas flow by providing broadly distributed radiant heat to the volatile carrier.

Alternatively, the holder can be in the form of an oven located within the heating chamber. "Oven" shall mean any substantially enclosed sub-chamber located within the heating chamber walls and made, preferably, of a heat-conductive material. The oven has oven walls and is positioned within the air-flow path. By this arrangement, the oven is heated by hot gases rising from the fuel burner. The oven holds a volatile carrier within the oven to receive heat radiating inwardly from the oven walls, an arrangement that provides for a more even heating of the volatile carrier. The oven preferably has openings sufficient to admit hot gases rising from the fuel burner so that they may directly contact the volatile carrier, and in any event has vents to allow volatile materials released from the volatile carrier to escape from the oven.

Although the fuel burner can be located beneath a heating chamber that has an open bottom, preferably the fuel burner is contained within the heating chamber itself. This arrangement contributes to the control and isolation of the convective flow of hot gases rising from the fuel burner and can also provide containment and protection for a burning flame. Thus, the walls of the heating chamber above the fuel burner can define the air flow path and limit the effects of breezes and other air movement external to the volatile dispenser.

It is sometimes desirable to reduce the temperature of the combustion products prior to their acting to heat the volatile carrier. To help achieve this the heating chamber walls can be equipped with cooling vents communicating with the air outside of the heating chamber to cause unheated air to be drawn into the heating chamber by the passing flow of heated gases, to mix with and partially cool the hot combustion products from the fuel burner prior to their reaching the carrier holder. The cooling vents can be provided at any point in the air flow path, but preferably they are located at a point in the chamber walls at or above the level of the fuel burner but beneath the level at which a volatile carrier is held.

Although the fuel burner may burn fuel catalytically or otherwise without a flame and still fall within the breadth and scope of the invention, it is highly preferred that the fuel burner support a luminous flame positioned within the heating chamber and that the heating chamber walls include a light-transmitting portion, whether clear or translucent, that allows light from the flame to be visible to a user of the dispenser. This provides a ready means for a user to confirm that the fuel burner has been lit and continues to burn, and it also provides a use-up cue for the fuel. But, more importantly, the flame provides light and aesthetic appeal, in much the same way that a citronella candle is valued in great part for its light. However, it is preferred that the carrier holder be positioned within a portion of the heating chamber whose walls are opaque so that the holder is not visible through the chamber side walls.

The mats or other volatile carriers become exhausted and are designed to be replaced. To achieve this an insert slot communicates between the interior of the heating chamber and the exterior of the heated volatile dispenser, so that a fresh volatile carrier can be inserted through the insert slot to be held by the carrier holder. The insert slot can be in either the chamber walls or the ceiling of the heating chamber.

It can be important to prevent the use of a volatile carrier not intended for use with a particular volatile dispenser, to not mistakenly use, for example, a volatile carrier loaded with insecticide in a dispenser intended to supply perfume for indoor use. Therefore, it is preferred that the insert slot include keying structures that impart a cross-sectional profile to the insert slot that so restricts access thereto as to prevent the insertion of any volatile carrier not capable of presenting a non-interfering cross-sectional profile to the cross-sectional profile of the insert slot. This makes it easier to ensure that only volatile carriers will fit a dispenser that are appropriate to a particular purpose or that are designed for use with the specific temperatures generated by the volatile dispenser. Also, the keying structures can be used to require that the volatile carrier be insertable only with a pre-determined side up or down. This can be important if the volatile carrier is, by way of example only, a gel cup that must be inserted so as to open upwardly. As examples, the keying structures can define a cross-sectional profile that includes either or both of angularly intersecting and curved sections.

Volatile carriers have a section treated or loaded (e.g. paper impregnated with liquid insecticide) with the volatile material to be dispensed, and this section may itself be formed with a functionally required cross-sectional profile such as those just described. Alternatively, the volatile carrier can include a handle in addition to a volatile-treated section, and the keying structures of the insert slot can be formed to present a non-interfering cross-sectional profile with respect to at least a portion of the volatile carrier and an interfering cross-sectional profile with respect to the handle for the volatile carrier.

In one embodiment, the heated volatile dispenser includes a fuel tank, containing fuel under pressure, and a fuel transfer route by which fuel can be transferred to the fuel burner in controlled amounts. Valves, constricted flow paths, wicks, pressure step-down controllers, or any other means may be used to control the delivery of pressurized fuel to the fuel burner in an amount sufficient to maintain combustion at a convenient level, and a variable valve may be used to allow a user to adjust the amount of fuel being burned. Preferably the fuel tank is replaceably removable. Ideally, the fuel tank contains fuel that burns as a pressurized gas, even though it may be a liquid at the tank pressures selected. Preferred gases include a gas selected from the group consisting of butane, isobutane, propane, compressed natural gas, and mixtures thereof.

An alternative embodiment of the heated volatile dispenser of the invention is designed for use with a volatile carrier having a volatile-loaded section having a linearly extended volatile-releasing surface. The heated volatile dispenser includes a heat source that preferably is a fuel burner, the heat source generating a convective flow of hot gases, and a carrier holder that holds the volatile carrier within the flow of hot gases in an orientation such that hot gas sweeps over the volatile-releasing surface in a generally vertical direction generally parallel to the direction of linear extension of the volatile-releasing surface to release volatile therefrom. The heated volatile dispenser can also have any or all of the other features described, above.

Preferably a volatile carrier is used that has at least two volatile-releasing surfaces. The carrier holder then is designed to hold the volatile carrier in an orientation such that hot gas sweeps over at least two of the volatile-releasing surfaces at the same time. Most conveniently, the volatile carrier has front and back volatile-releasing surfaces. By way of example, only, a conventional mosquito mat has front and back surfaces, and the carrier holder can be designed to hold a mat edge-on with respect to the flow of hot gases so that gas sweeps over both surfaces of the mat at the same time.

This arrangement has important advantages for the control of temperature across the volatile-releasing surfaces of the volatile carrier. The convective flow of hot gases above a sufficiently hot heater, and especially above a fuel burner that produces both heat and gaseous combustion products, is fast compared to the conductive flow of heat through metal. Consequently, it is believed that the temperature of the hot gases does not drop much as the gases pass over the volatile-releasing surfaces. As a result, the volatile carrier is more evenly heated across its linear expanse so that volatiles are released more uniformly from the entire volatile-releasing surface. When the rate of volatile release from the volatile carrier drops sufficiently low that a fresh carrier is needed, the volatile from the exhausted carrier will have been more completely used than is the case when distinct hotter and cooler regions are formed across the volatile-releasing surfaces.

When the heated volatile dispenser is designed to be used with a volatile carrier having a linearly extended, volatile treated section having a leading edge to be presented toward the flow of hot combustion products, the carrier holder should usually include a heat resistant edge guard that extends along the leading edge of a volatile carrier held in the carrier holder. The edge guard preferably extends the entire length of the leading edge. Alternatively, the edge guard can extend to protect only a portion of the leading edge that is exposed to the hottest area within the flow of hot combustion products, typically located at the center of the leading edge. An edge guard will be understood to be "heat resistant" if it does not burn, char, or deform when subjected to the temperatures present at its location within a heated volatile dispenser when that dispenser is in use.

The edge guard protects the leading edge of the volatile carrier from heat directly radiating from fuel burner and from direct, edgeward impact of the flow of hot gases. Also, when the carrier holder has at least two and preferably a front and back volatile-releasing surface, the edge guard helps to split the flow of hot gases to direct the gases across the volatile-releasing surfaces. Either additionally or alternatively, a volatile carrier of the invention intended for such an edge-on orientation can be equipped with a carrier edge guard formed on or attached to the leading edge of the volatile carrier, itself. It is preferred that the edge guard, whether a part of the heated volatile dispenser or attached to the leading edge of the volatile carrier, include deflector vanes extending sidewardly with respect to the direction of linear extension of the volatile carrier's treated section to disrupt and mix the flow of hot gases before the gases contact the treated section.

A method of the present invention for dispensing ingredients volatilizable by application of heat includes a first step of providing a heated volatile dispenser having (a) a heating chamber having chamber walls and a ceiling with exit vents in either the ceiling or chamber walls communicating between the interior of the heating chamber and the outside air, (b) a fuel burner, (c) a carrier holder to receive and hold a volatile carrier in a location above the fuel burner and contained within the heating chamber, and (d) an air-flow path to guide hot gases from the fuel burner, preferably including combustion products, to direct contact with a volatile carrier held by the carrier holder, the air-flow path being adapted to then direct the hot gases to an exit vent to pass out of the dispenser. A further step of the method is to position in the carrier holder a volatile carrier loaded with the ingredients to be volatilized. A yet further step is to ignite the fuel. This step may be performed either before or after the step of positioning of the volatile carrier in the carrier holder. A final step is to allow the volatile carrier to be heated and the ingredients thus volatilized therefrom to be vented from the dispenser.

An alternative method of the invention for dispensing a volatile material from a volatile carrier having a volatile-loaded section having a linearly extended, volatile-releasing surface includes a first step of providing a heat source, preferably a fuel burner, generating a flow of hot gases and a second step of holding the volatile carrier within the flow of hot gases in an orientation such that hot gas sweeps over the volatile-releasing surface in a direction generally parallel to the direction of linear extension of the volatile-releasing surface. Preferably, the volatile carrier has at least two and preferably both front and back volatile-releasing surfaces and the step of holding the volatile carrier within the flow of hot gases includes holding the volatile carrier in an orientation such that hot gas sweeps over at least two and preferably both the front and back volatile releasing surfaces at the same time.

The invention also includes a volatile-dispensing volatile carrier suitable for use with a heated volatile dispenser having an insert slot through which the volatile carrier must be inserted for use, the insert slot having keying structures that impart a cross-sectional profile to the insert slot that departs from a straight cross-sectional profile and that so restricts access thereto as to prevent the insertion of any volatile carrier not capable of presenting a complementary cross-sectional profile. The volatile carrier of the invention includes a treated section having a cross-sectional profile complementary to that of the insert slot. The volatile carrier also can have a handle having a cross-sectional profile that prevents the handle's entrance into the insert slot. Preferably the cross-sectional profile of the treated section includes curved or angularly intersecting sections, the latter including (without limitation) slots, prongs, ribs, and the like. Combinations of curved and angularly intersecting sections may also be used. Preferably the volatile carrier is a mat.

DETAILED DESCRIPTION OF THE INVENTION

Figure 1:
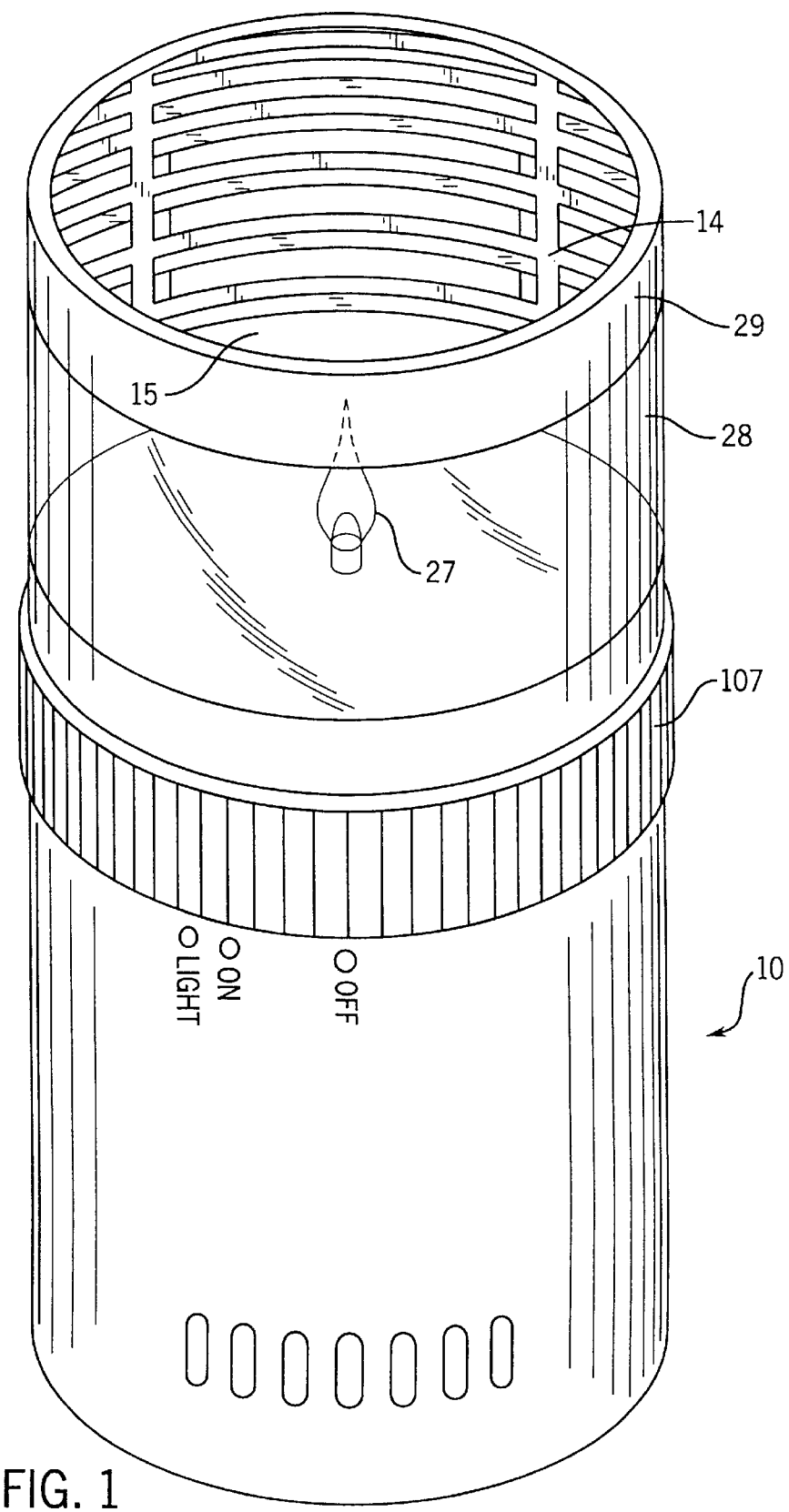
FIG. 1 is a perspective view of a heated volatile dispenser of the invention which uses a gas fuel source.
Figure 2:
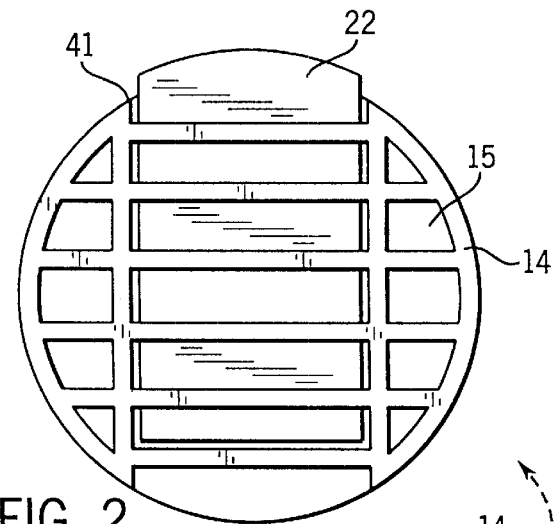
FIG. 2 is a top plan view thereof.
Figure 3:
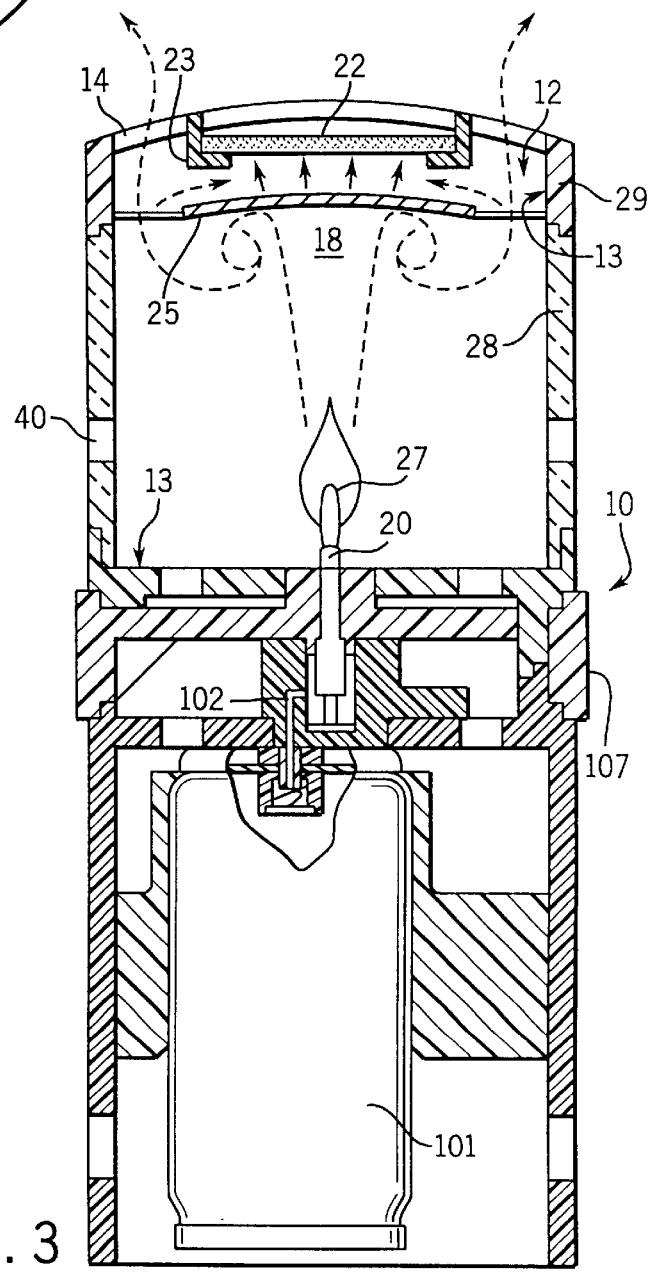
FIG. 3 is a vertical cross sectional view of the FIG. 1 embodiment.

We turn first to the embodiment of FIGS. 1–4. A dispenser, generally 10, encloses an internal heating chamber 12 having chamber side walls 13. There is also a chamber ceiling 14 that has exit vents 15.

The assembly includes a fuel burner 20. Fuel is supplied from a pressurized gas fuel source 101 through a fuel transfer route 102 by which fuel can be transferred to the fuel burner 20 in controlled amounts. Various types of valving and ignition systems can be used for this purpose (see e.g. U.S. Pat. No. 5,700,430).

Figure 4:
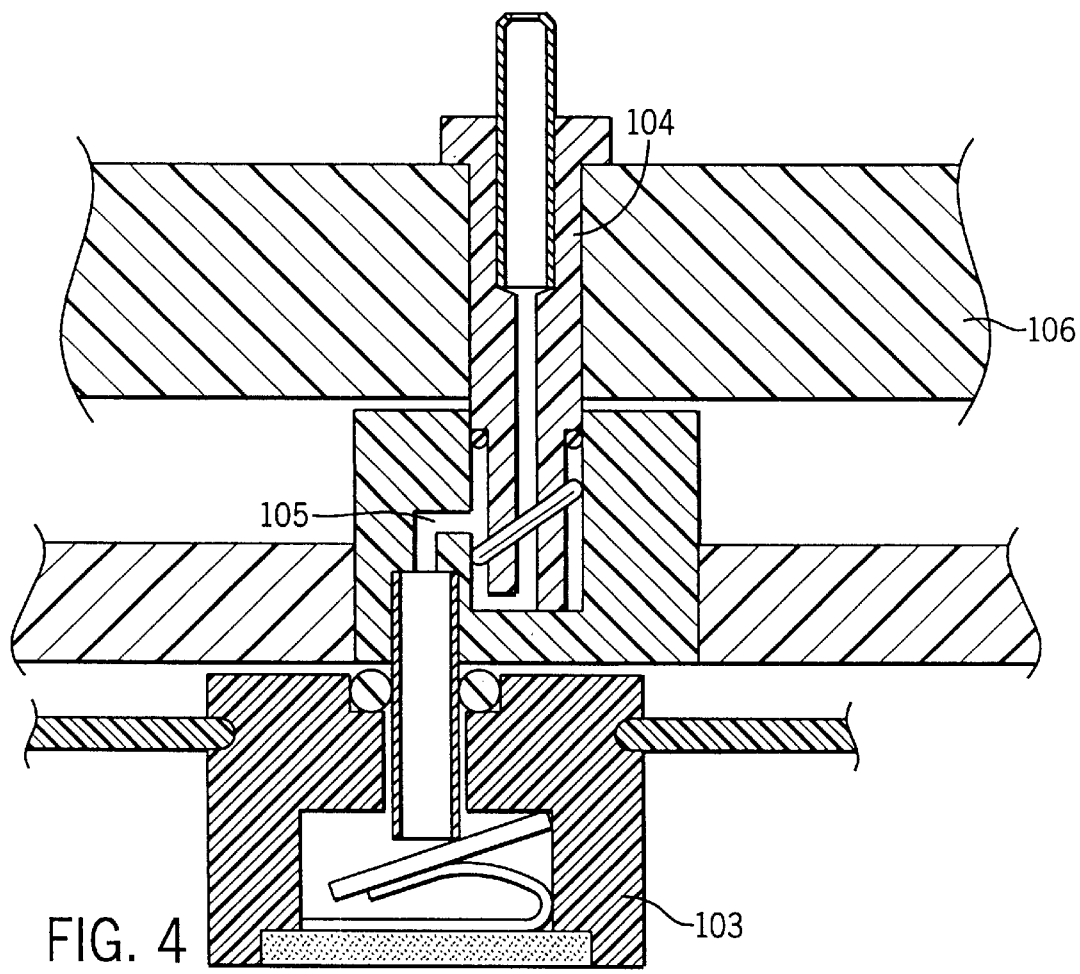
FIG. 4 is an enlarged cross sectional view of the shut-off valve portion of FIG. 3.

However, another option is depicted in FIGS. 1 and 4. Rotation of outer ring 107 will cause rotation of inner ring 106, thereby rotating a lower extension therefrom, which acts as a valve to control the amount of fuel being provided. Various known ignition systems, not shown, can be incorporated as well.

The dispenser also includes a cellulosic mat-like carrier 22, preferably impregnated with an insect control ingredient, preferably an insecticide. The carrier is slid through insert slot 41 in the outer housing and rests on carrier holder 23. The carrier holder 23 is located above the fuel burner and within the heating chamber 12.

The walls of the chamber provide an air-flow path to guide hot combustion products from the fuel burner 20 past the carrier holder 23 to heat the carrier 22. This provides the direct exposure of the volatile carrier to the combustion products created by the flame 27.

Preferably there is also a baffle 25 interposed between the fuel burner 20 and the carrier 22. This creates turbulence in the region 18 so as to better mix combustion products prior to their reaching the carrier 22. The baffle 25 also acts as a radiant heater beneath the carrier holder 23.

There is a light transmitting transparent plastic portion 28 which allows light from the flame 27 to be visible to a user of the dispenser. Thus, the dispenser both dispenses the volatile and provides a light function. In this form, the fuel burner 20 is preferably also within the heating chamber 12.

There may also be a cooling vent 40 that permits air outside of the heating chamber 12 to enter the heating chamber and partially cool the hot combustion products prior to their reaching the carrier. Vent 40 is located above the level of the fuel burner.

The carrier holder 23 is positioned within a part 29 of the heating chamber 12 that is either opaque or translucent such that the carrier holder is not visible through the chamber side walls. It is preferred that the wall portions 28 and 29 be permanently assembled together (e.g. sonic welded) so that the heating chamber remains continuously enclosed.

Figure 5:
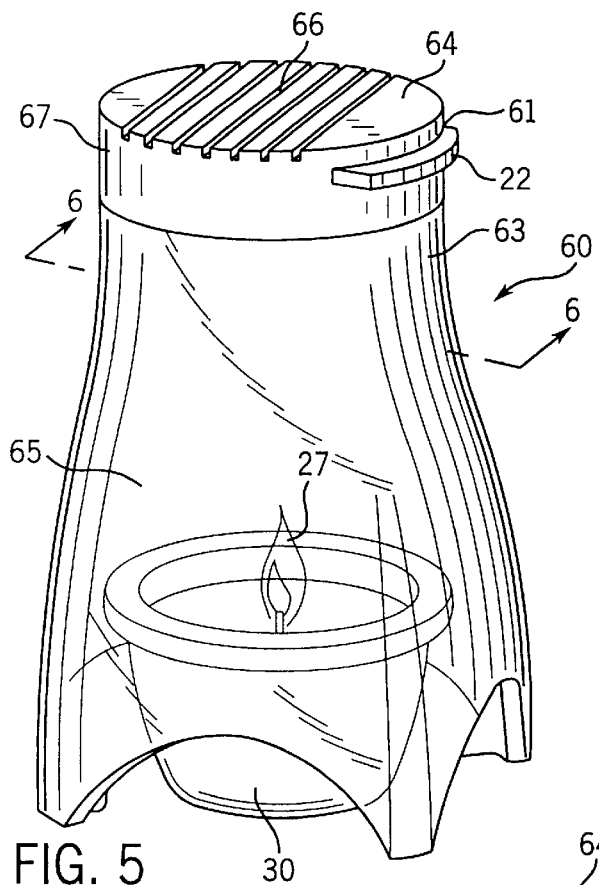
FIG. 5 is a perspective view of a second embodiment of the invention which uses a candle for fuel.
Figure 6:
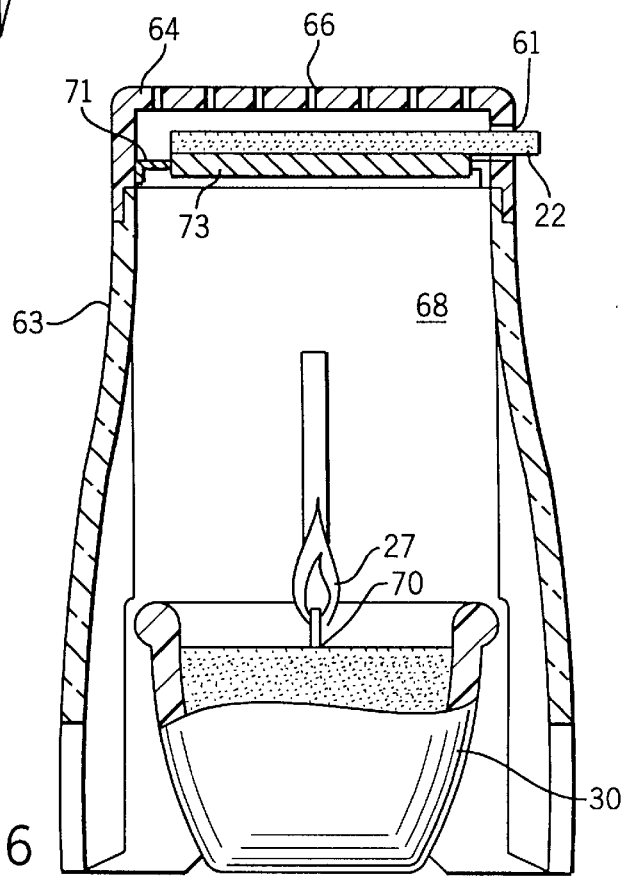
FIG. 6 is a cross sectional view of the embodiment of FIG. 5 taken along line 6—6 of FIG. 5.
Figure 7:
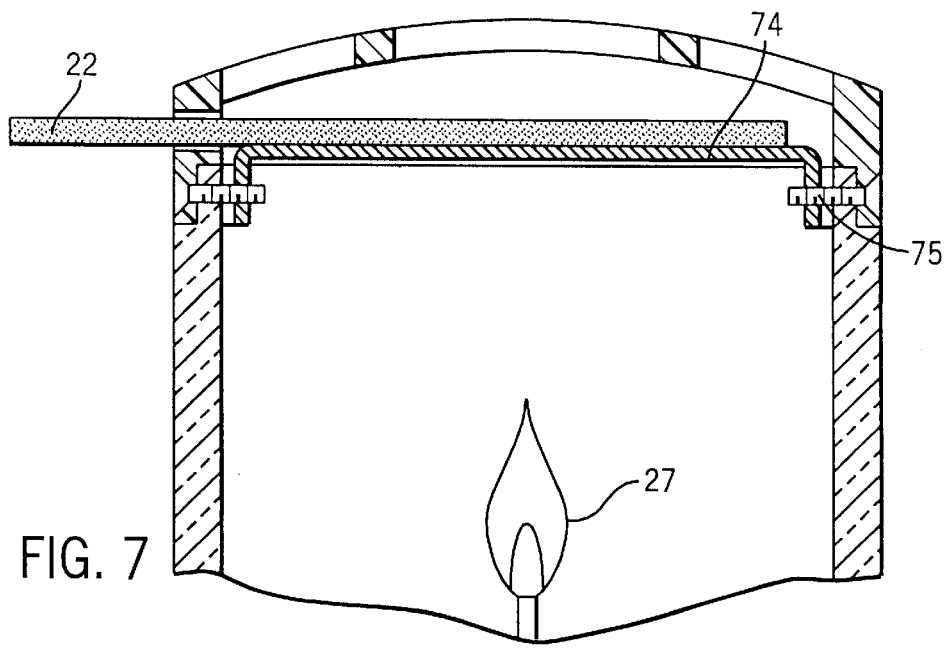
FIG. 7 is a cross sectional view of the upper portion of a heated volatile dispenser like that of FIG. 1 or FIG. 5, albeit showing an alternative carrier holder having a conductive sole plate.

Turning next to the embodiment of FIGS. 5–7 (generally 60), the fuel burner is now the wick of wax candle 30. There is a housing 65 with a cap 64 having vents 66. Side walls 63 help define the heating chamber. The volatile carrier 22 is inserted through slot 61 and in this case held on a sole plate 73 that is solid except for having spider leg radially peripheral attachments 71. The housing 65 can be lifted off the candle 30, the candle can be lit with a match, and the housing can be replaced to its FIG. 5 position.

In either case (the FIG. 1 or the FIG. 5 embodiment), the combustion products flow upward and ultimately around the volatile carrier before exiting. The combustion products will be sufficiently dispersed so as to provide desirable heating. The same flame which provides the heat source will also provide the light source.

Turning now to FIG. 7, another version of the sole plate 74 has its ends alternatively supported in side brackets 75. The design is otherwise similar to the embodiment of FIG. 5.

Figure 8:
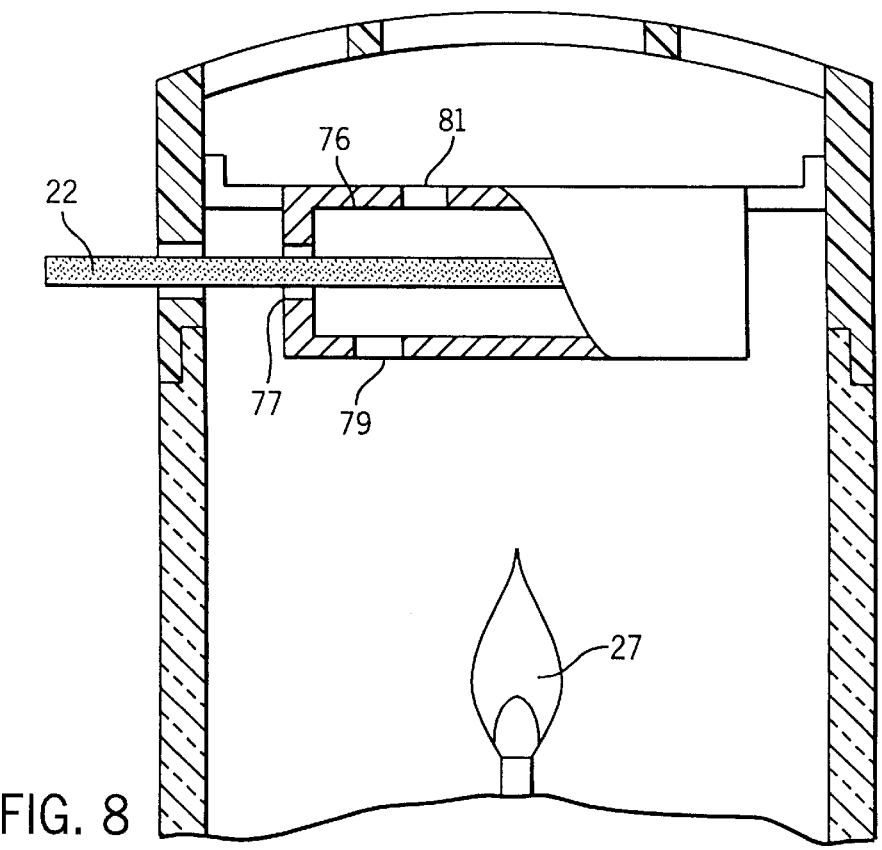
FIG. 8 is a cross sectional view of the upper portion of a heated volatile dispenser like that of FIG. 1 or FIG. 5, albeit showing another alternative volatile carrier holder in the form of an oven.

As shown in FIG. 8, there is provided an oven (generally 76). It has a side slot 77 that is aligned with the outer insert slot so as to permit the carrier 22 to be inserted not only through the outer insert slot, but also in the oven. In use, the oven 76 has a sufficient heat capacity that it serves to maintain a more constant temperature within the oven than might otherwise be experienced at that location in the flow of hot, gaseous combustion products if, for example, the heat source were a flickering flame. Bottom hole 79 permits combustion products to readily enter the oven. Top hole 81 permits them to readily exit.

Figure 9:
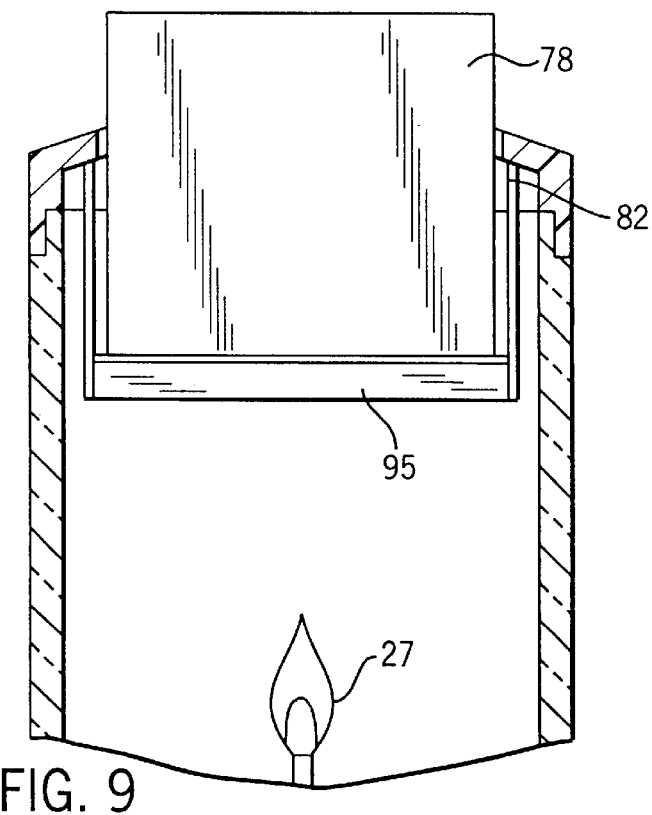
FIG. 9 is a cross sectional view of the upper portion of a heated volatile dispenser like that of FIG. 1 or FIG. 5, albeit showing another alternative volatile carrier holder that holds a volatile carrier in a vertical orientation.
Figure 10:
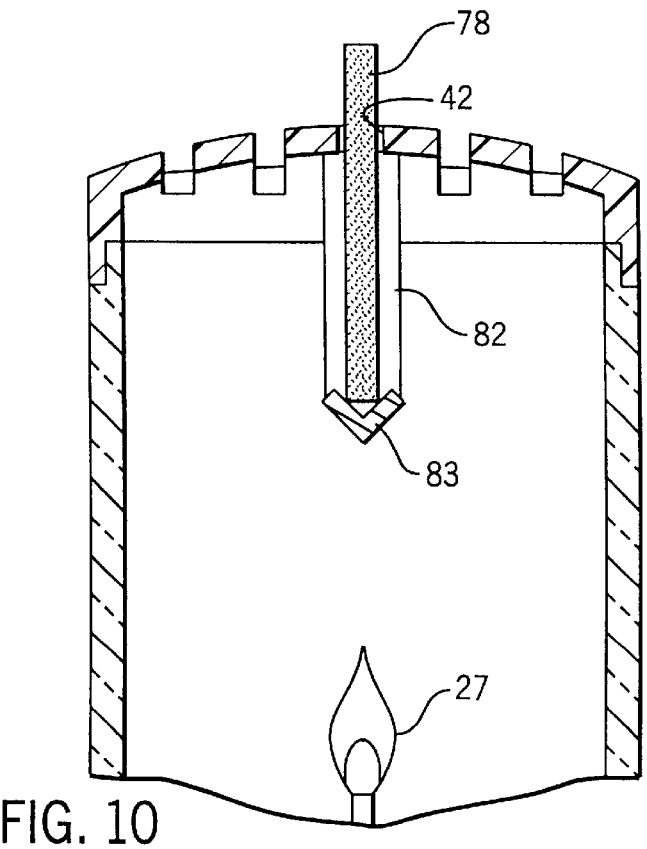
FIG. 10 is a partial cross sectional view of the heated volatile dispenser of FIG. 9, albeit taken at an angle which is rotated 90 degrees relative to that of FIG. 9.

FIGS. 9 and 10 depict the use of a generally vertically positioned carrier 78 inserted through an insert slot 42 and held by a carrier 82 having a protective guard 83 with side walls 95. This system has the advantage of exposing both sides of the carrier to roughly equivalent heat. The hot gas sweeps over the volatile-releasing surface in a direction generally parallel to the direction of linear extension of the volatile-releasing surfaces. Yet, the downward edge is protected against undesirable overheating by a lower guard.

Figure 11:
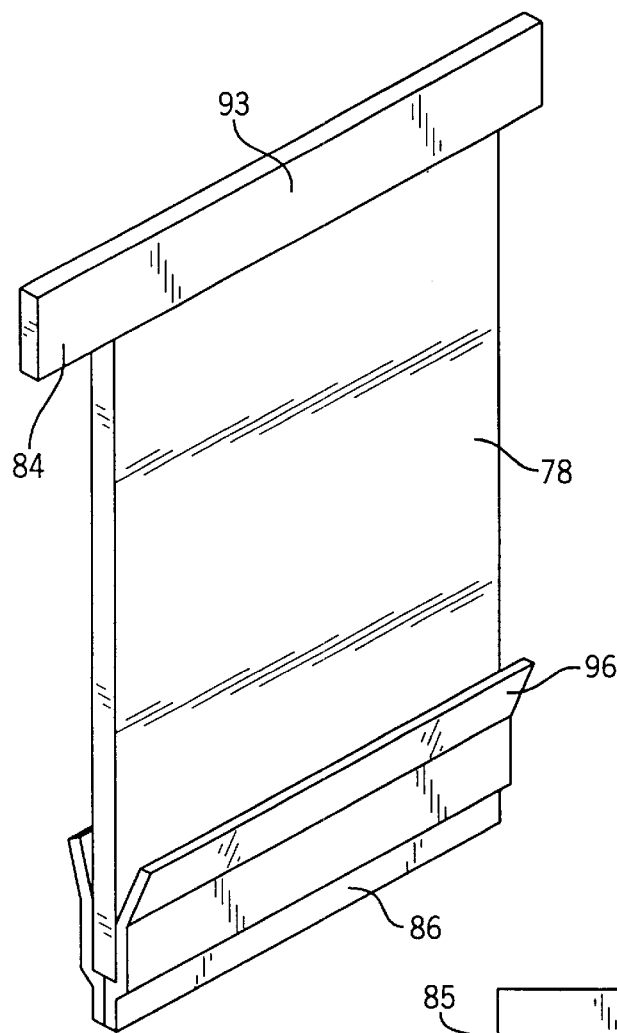
FIG. 11 is a perspective view of another volatile carrier of the invention having an edge guard.
Figure 12:
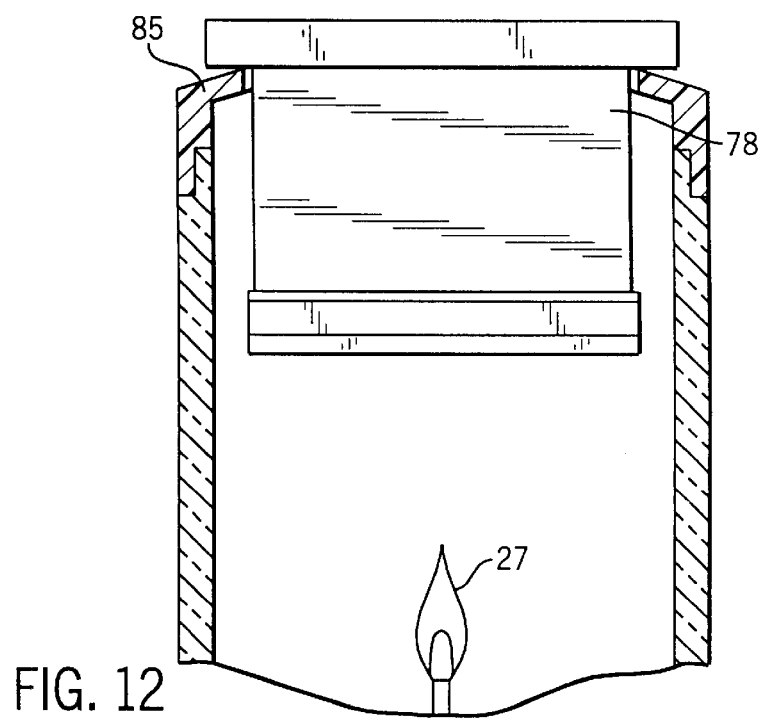
FIG. 12 is a cross sectional view generally corresponding to FIG. 9, but showing how surfaces of the heating chamber ceiling can serve as the carrier holder.

As shown in FIG. 11, the carrier 78 can be provided with a handle 93 and a heat resistant guard 86 positioned on a leading edge so as to be able to split the flow of hot gasses when the carrier is held within the flow of hot gasses. This again protects the treated section from edgeward impact of the hot gasses. The guard preferably also has deflector vanes 96 extending sidewardly.

In these vertical forms, the carrier 78 is linearly extended and treated on both front and back sides.

Figure 15:
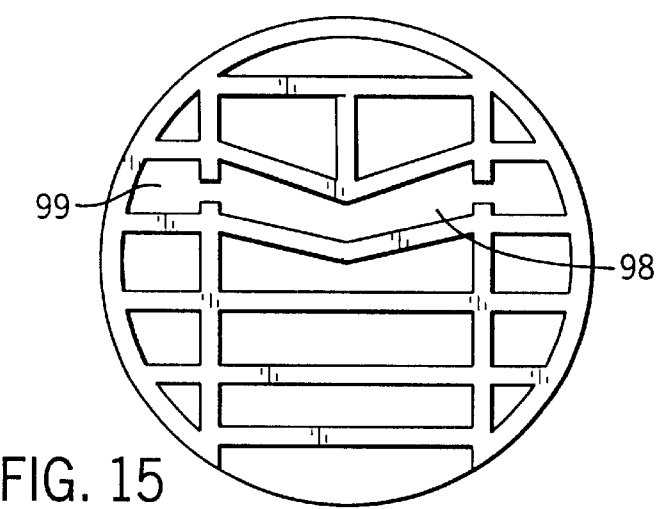
FIG. 15 is a top plan view of a dispenser having a ceiling with an insert slot suitable to receive the FIG. 13 volatile carrier.
Figure 13:
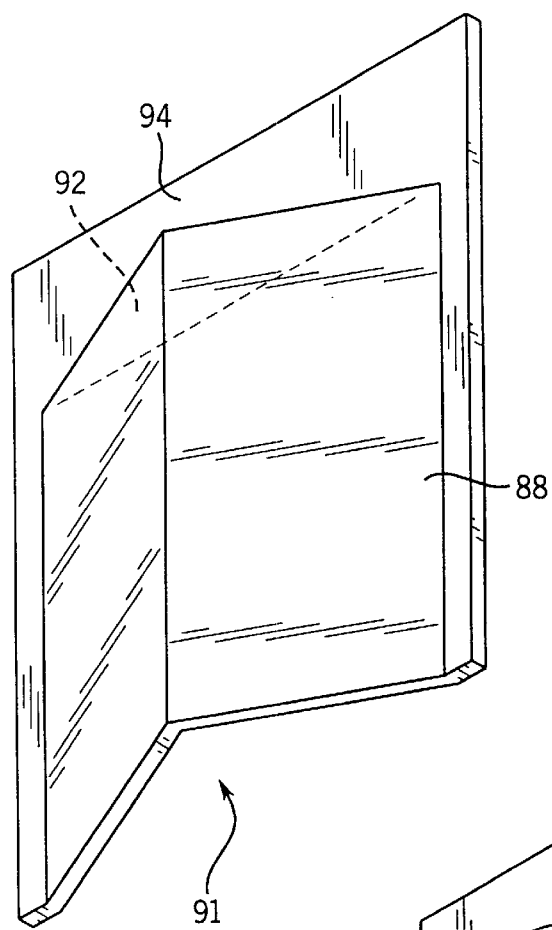
FIG. 13 is a lower frontal perspective view of a form of volatile carrier that can be used when the top of the FIG. 9 embodiment is provided with the FIG. 15 inlet slot.

As best seen in FIG. 15, an insert slot 98 (which is not simply rectangular) can be formed in the ceiling of the dispenser. When used with a carrier such as carrier 88 of FIG. 13, the edge 91 presents a non-interfering cross-sectional profile with respect to the insert slot 98, while still allowing some venting via exits 99. The opposite surface from surface 92 shown presents an interfering cross-sectional profile preventing the handle 94 from falling through the insert slot.

Figure 14:
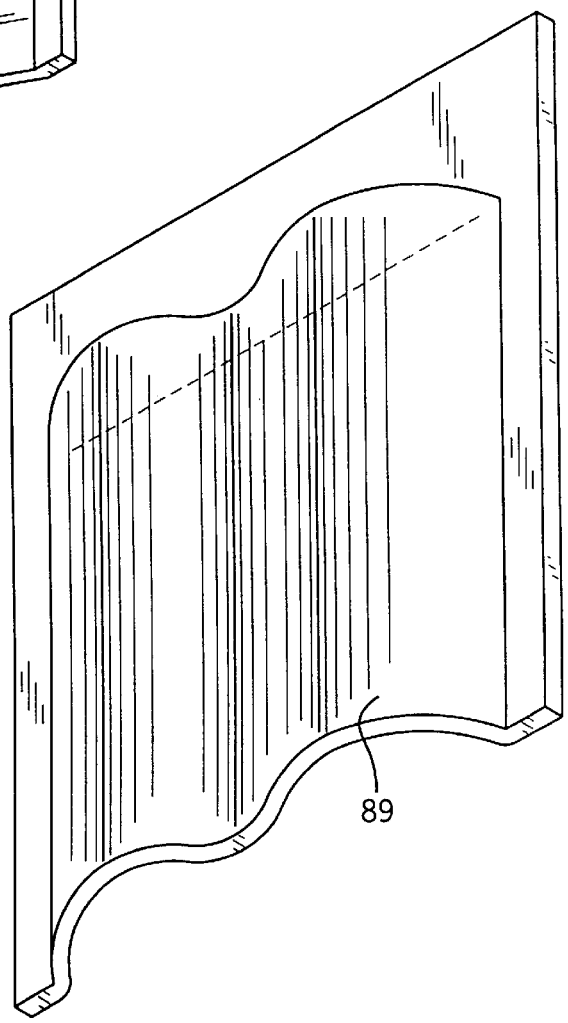
FIG. 14 is a lower frontal perspective view of another form of volatile carrier that can be used when the top of the FIG. 9 embodiment is provided with a wavy curve inlet slot.

If instead the carrier is carrier 89 as shown in FIG. 14, the FIG. 15 insert slot would then need to be a wavy line inlet. Thus, by using either form, the proper direction of the carrier can be controlled, and the public can be prevented from inserting standard rectangular mats into the system which are not appropriate for use with this system.

In essence, this is a keying structure in which the cross-sectional profile of the insert slot must match with the cross-sectional profile of an inward end of the volatile carrier. The profile should depart from a rectangular slot, preferably using angularly intersecting and/or curved sections. Moreover, such a system is particularly useful in connection with horizontally extending carriers that have only one side treated with active.

The various parts of the dispenser described above can be manufactured by conventional means from heat-resistant plastics, metal, glass, and the like. The volatile carriers disclosed can be made using conventional methods and materials well known in the art, such as those used for making conventional mosquito mats, volatile gel carriers, volatile-containing polymers, and the like.

The preceding description is merely of preferred embodiments of the invention. One skilled in the art will readily apprehend alternative embodiments that nevertheless fall within the scope and breadth of the invention. Thus, the claims should be looked to in order to understand the full scope of the invention.

INDUSTRIAL APPLICABILITY

Heated volatile dispensers and volatile carriers, and methods of using them, are described. They are useful in the practical control of insects and other pests and in air scenting.

We claim:
1. A heated volatile dispenser, comprising:
 a. an enclosed heating chamber having chamber walls, a ceiling, and an exit vent in at least one of the chamber walls and ceiling, the exit vent communicating between the interior of the heating chamber and the outside air;
 b. a fuel burner;
 c. a carrier holder positioned to receive and hold a volatile carrier in a location above the fuel burner and contained within the heating chamber; and
 d. an air-flow path to guide hot gases with hot combustion products from the fuel burner past the carrier holder to heat a volatile carrier held thereby by the direct exposure of the volatile carrier to the hot gases with hot combustion products, the air-flow path then directing the hot gases with hot combustion products through the exit vents to escape from the dispenser.

2. The heated volatile dispenser of claim 1 further comprising a baffle interposed between the fuel burner and the carrier holder to create turbulence that mixes the hot gases with hot combustion products from the fuel burner prior to their reaching the carrier holder.

3. The heated volatile dispenser of claim 2 wherein the carrier holder is spaced above the baffle and the baffle is so located as to be heated by the hot gases with hot combustion products contacting the baffle from below, the hot baffle serving as a radiant heater beneath the carrier holder.

4. A heated volatile dispenser, comprising:
   a. an enclosed heating chamber having chamber walls, a ceiling, and an exit vent in at least one of the chamber walls and ceiling, the exit vent communicating between the interior of the heating chamber and the outside air;
   b. a fuel burner;
   c. a volatile carrier;
   d. a carrier holder positioned to receive and hold the volatile carrier in a location above the fuel burner and contained within the heating chamber; and
   e. an air-flow path to guide hot gases with hot combustion products from the fuel burner past the carrier holder to heat a volatile carrier held thereby by the direct exposure of the volatile carrier to the hot gases with hot combustion products, the air-flow path then directing the hot gases with hot combustion products through the exit vents to escape from the dispenser;
   wherein the fuel burner supports a flame positioned within the heating chamber and the heating chamber walls include a light-transmitting portion that allows light from the flame to be visible to a user of the dispenser through the light-transmitting portion.

5. The heated volatile dispenser of claim 4 wherein the fuel burner is also contained within the heating chamber.

6. The heated volatile dispenser of claim 5 wherein a heating chamber wall has a cooling vent communicating with air outside of the heating chamber to cause unheated air to enter the heating chamber to mix with and partially cool the hot gases with hot combustion products from the fuel burner prior to their reaching the carrier holder.

7. The heated volatile dispenser of claim 6 wherein the cooling vent is located at a point in the chamber wall above the level of the fuel burner.

8. The heated volatile dispenser of claim 4 wherein
   a. the walls of a part of the heating chamber are selected from the group consisting of opaque and translucent, and
   b. the carrier holder is positioned within that part of the heating chamber so that the carrier holder is not visible through chamber side walls.

9. The heated volatile dispenser of claim 4 wherein the carrier holder comprises a heat-conductive sole plate that supports the volatile carrier.

10. The heated volatile dispenser of claim 4 wherein an insert slot communicates between the interior of the heating chamber and the exterior of the heated volatile dispenser, through which insert slot a volatile-bearing volatile carrier may be inserted to be held by the carrier holder.

11. The heated volatile dispenser of claim 10 wherein the insert slot includes keying structures that impart a cross-sectional profile to the insert slot that so restricts access thereto as to prevent the insertion through the slot of any volatile carrier not capable of presenting a non-interfering cross-sectional profile to the cross-sectional profile of the insert slot.

12. The heated volatile dispenser of claim 11 wherein the keying structures define a cross-sectional profile selected from the group consisting of angularly intersecting and curved sections.

13. The heated volatile dispenser of claim 10 wherein the insert slot extends through a ceiling of the heating chamber.

14. The heated volatile dispenser of claim 10 wherein the volatile carrier includes a treated section loaded with the volatile material to be dispensed and a handle, and wherein the keying structures of the insert slot present an interfering cross-sectional profile with respect to a portion of the handle.

15. The heated volatile dispenser of claim 4, wherein the carrier holder is in the form of an oven located within the heating chamber, the oven having oven walls and being positioned within the air-flow path so as to be heated by the hot gases rising from the fuel burner, the oven having openings sufficient to admit the hot gases rising from the fuel burner and having vents to allow the escape therefrom of volatile materials.

16. The heated volatile dispenser of claim 4 wherein the fuel burner is selected from the group consisting of a candle, a solidified combustible liquid, a burnable solid, a catalytic heater, a pressurized gas burner, and a wick that is fueled with a combustible liquid.

17. The heated volatile dispenser of claim 4 further comprising:
   a. a fuel tank containing fuel under pressure; and
   b. a fuel transfer route by which fuel can be transferred to the fuel burner in controlled amounts.

18. A volatile carrier suitable for use with a heated volatile dispenser that has an insert slot through which the volatile carrier can be inserted to load the heated volatile dispenser, the insert slot having keying structures that impart to it a cross-sectional profile that departs at least in part from a rectangular opening and that so restricts access thereto as to prevent loading through the slot any volatile carrier not having a complementary cross-sectional profile to the insert slot, the volatile carrier comprising:
   a. a treated section loaded with the volatile material to be dispensed;
   b. an end with a cross-sectional profile that departs from rectangular; and
   c. at least one surface presenting an interfering cross-sectional profile with respect to the insert slot.

19. A volatile carrier suitable for use with a heated volatile dispenser designed to expose a volatile carrier to a flow of hot gases, the volatile carrier comprising
   a. a treated section that is linearly extended and is loaded with the volatile material to be dispensed, the treated section having front and back sides and a leading edge; and
   b. a heat-resistant edge guard positioned on the leading edge to split the flow of hot gases when the volatile carrier is held within a flow of hot gases with the leading edge presented toward the hot gas flow to direct the hot gases over both the front and back sides, and to assist in protecting the treated section from direct, edgeward impact from the hot gases.

20. The volatile carrier of claim 19 wherein the edge guard has deflector vanes extending sidewardly with respect to the direction of linear extension of the treated section.

21. A method for dispensing ingredients volatilizable by application of heat, the method comprising the steps of:
   a. providing a heated volatile dispenser having:
      i. a heating chamber having chamber walls, a ceiling, and an exit vent in at least one of the chamber walls and ceiling, the exit vent communicating between the interior of the heating chamber and the outside air;

ii. a fuel burner;

iii. a carrier holder to receive and hold a volatile carrier in a location above the fuel burner and contained within the heating chamber; and iv. an air-flow path to guide hot gases with hot combustion products from the fuel burner into direct contact with a volatile carrier held by the carrier holder, and then to vent the hot gases with hot combustion products from the dispenser;

b. positioning in the carrier holder a volatile carrier loaded with ingredients to be volatilized;

c. igniting fuel at the fuel burner; and d. allowing the volatile carrier to be heated and the ingredients thus volatilized therefrom to be vented from the dispenser.

22. A heated volatile dispenser for use with a volatile carrier having a volatile-loaded section having a linearly extended, volatile-releasing surface, the heated volatile dispenser comprising:

a. a fuel burner generating hot gases;

b. a carrier holder that can hold the volatile carrier with the volatile-loaded section above the fuel burner and within the hot gases in an orientation such that hot gas sweeps over the volatile-releasing surface in an essentially vertical direction essentially parallel to the direction of linear extension of the volatile-releasing surface to release volatile therefrom.

23. The heated volatile dispenser of claim 22 for use with a volatile carrier having at least two volatile-releasing surfaces and wherein the carrier holder can hold the volatile carrier in an orientation such that hot gas sweeps over at least two of the volatile-releasing surfaces at the same time.

24. The heated volatile dispenser of claim 22 further comprising:

a. a heating chamber within which the carrier holder positions the volatile carrier, the heating chamber having chamber walls, a ceiling, and exit vents in at least one of the chamber walls and ceiling, the exit vents communicating between the interior of the heating chamber and the outside air; and b. an air-flow path to guide hot combustion products from the fuel burner to directly contact the volatile-releasing surface of the volatile carrier, the hot combustion products then being vented from the dispenser.

25. The heated volatile dispenser of claim 24 for use with a volatile carrier having a linearly extended, volatile treated section having a leading edge to be presented toward the flow of hot combustion products, the carrier holder including a heat resistant edge guard suitable to extend along the leading edge of a volatile carrier when the volatile carrier is held in the carrier holder.

26. The heated volatile dispenser of claim 24 further comprising a baffle interposed between the fuel burner and the carrier holder to create turbulence that mixes hot combustion products from the fuel burner prior to their reaching the carrier holder.

27. The heated volatile dispenser of claim 24 wherein the heating chamber walls have cooling vents communicating with the air outside of the heating chamber to cause unheated air to enter the heating chamber to mix with and partially cool the hot combustion products from the fuel burner prior to their reaching the carrier holder.

28. The heated volatile dispenser of claim 27 wherein the cooling vents are located at a point in the chamber walls above the level of the fuel burner.

29. The heated volatile dispenser of claim 24 wherein the fuel burner supports a flame located within the heating chamber and the heating chamber walls include a light-transmitting portion that allows light from the flame to be visible to a user of the dispenser.

30. The heated volatile dispenser of claim 29 wherein a. the walls of a part of the heating chamber are selected from the group consisting of opaque and translucent; and b. the carrier holder is positioned within that part of the heating chamber so that the carrier holder is not visible through the chamber walls.

31. The heated volatile dispenser of claim 24 wherein an insert slot communicates between the heating chamber and the exterior of the heated volatile dispenser, extending through one of the ceiling or the chamber walls, through which insert slot a volatile-bearing volatile carrier may be inserted to be held by the carrier holder.

32. The heated volatile dispenser of claim 31 wherein the insert slot includes keying structures that impart an at least partially non-rectangular cross-sectional profile to the insert slot that so restricts access thereto as to prevent the insertion of any volatile carrier not capable of presenting a cross-sectional profile complementary to the cross-sectional profile of the insert slot.

33. The heated volatile dispenser of claim 32 wherein the keying structures define a cross-sectional profile selected from the group consisting of angularly intersecting and curved sections.

34. The heated volatile dispenser of claim 24 wherein the fuel burner is selected from the group consisting of a candle, a solidified combustible liquid, a burnable solid, a catalytic heater, a pressurized gas burner, and a wick that is fueled with a combustible liquid.

35. A method of dispensing a volatile material from a volatile carrier having a volatile-loaded section having a linearly extended, volatile-releasing surface, the method comprising the steps of:

a. providing a fuel burner generating hot gases;

b. holding the volatile carrier with the volatile-loaded section above the fuel burner and within the hot gases in an orientation such that hot gas sweeps over the volatile-releasing surface in an essentially vertical direction essentially parallel to the direction of linear extension of the volatile-releasing surface.

36. The method of claim 35 wherein the volatile carrier has both front and back volatile-releasing surfaces and the step of holding the volatile carrier within the hot gases includes holding the volatile carrier in an orientation such that hot gas sweeps over both the front and back volatile releasing surfaces at the same time.

* * * * *

UNITED STATES PATENT AND TRADEMARK OFFICE
CERTIFICATE OF CORRECTION

PATENT NO.   : 6,503,459 B1
DATED        : January 7, 2003
INVENTOR(S)  : Stephen B. Leonard et al.

It is certified that error appears in the above-identified patent and that said Letters Patent is hereby corrected as shown below:

<u>Title page,</u>
Item [75], should read:

[75] Inventors:  Stephen B. Leonard, Caledonia, WI (US);
                 Scott W. Demarest, Caledonia, WI (US);
                 Michael C. Fryan, Mount Pleasant, WI (US);
                 Donald J. Shanklin, Fullerton, CA (US);
                 Paul E. Furner, Caledonia, WI (US);
                 Therese M. Nelson, Racine, WI (US) --

Signed and Sealed this

Twenty-seventh Day of April, 2004

JON W. DUDAS
*Acting Director of the United States Patent and Trademark Office*